(12) United States Patent
Damit et al.

(10) Patent No.: US 11,577,258 B2
(45) Date of Patent: Feb. 14, 2023

(54) CYCLONE AND METHODS OF MANUFACTURE THEREOF

(71) Applicant: The Johns Hopkins University, Baltimore, MD (US)

(72) Inventors: Brian E. Damit, Silver Spring, MD (US); Plamen A. Demirev, Ellicott City, MD (US); Elizabeth C. Corson, Columbia, MD (US); Felix C. Sage, Ijamsville, MD (US); Benjamin B. Alvarez, Hanover, MD (US); Charles A. Fancher, Baltimore, MD (US); Kelly A. Van Houten, West Friendship, MD (US); Christopher J. Rosenker, North Bethesda, MD (US)

(73) Assignee: The Johns Hopkins University, Baltimore, MD (US)

( * ) Notice: Subject to any disclaimer, the term of this patent is extended or adjusted under 35 U.S.C. 154(b) by 249 days.

(21) Appl. No.: 17/008,859

(22) Filed: Sep. 1, 2020

(65) Prior Publication Data

US 2021/0316318 A1 Oct. 14, 2021

Related U.S. Application Data

(60) Provisional application No. 62/930,636, filed on Nov. 5, 2019.

(51) Int. Cl.
*B04C 5/04* (2006.01)
*B04C 5/081* (2006.01)
(Continued)

(52) U.S. Cl.
CPC .............. *B04C 5/081* (2013.01); *B04C 5/04* (2013.01); *B04C 5/20* (2013.01); *G01N 1/2211* (2013.01);
(Continued)

(58) Field of Classification Search
CPC .. B04C 5/081; B04C 5/04; B04C 5/20; G01N 1/2211; G01N 1/4077; G01N 33/0011
See application file for complete search history.

(56) References Cited

U.S. PATENT DOCUMENTS

| 3,199,269 A | * | 8/1965 | Oehlrich | B04C 5/12 96/372 |
| 3,898,068 A | * | 8/1975 | McNeil | B04C 5/10 55/459.1 |

(Continued)

FOREIGN PATENT DOCUMENTS

| CN | 1471434 A | * | 1/2004 | ............ B04C 5/081 |
| CN | 110013921 A | * | 7/2019 | |

(Continued)

OTHER PUBLICATIONS

Bhardwaj, P., et al., "Microfluidic device based on a micro-hydrocyclone for particle-liquid separation," Lab Chip, vol. 11, 2011, pp. 4012-4021.

(Continued)

*Primary Examiner* — Dung H Bui
(74) *Attorney, Agent, or Firm* — Noah J. Hayward

(57) ABSTRACT

A cyclone includes a hollow cylindrical upper portion and a hollow conical lower portion having an inclined wall and a base wall. The base wall and the inclined wall are continuous contact with each other, and the inclined wall of the hollow conical lower portion is in continuous contact with an outer wall of the hollow cylindrical upper portion. A total cyclone height is from about 10 to about 30 millimeters, and a ratio of the total cyclone height to an inner diameter of the hollow cylindrical upper portion is from about 0.7 to about 1.3. An angle between an inner surface of the base wall and an inner surface of the inclined wall is from about 110 to about 130 degrees.

17 Claims, 3 Drawing Sheets

(51) Int. Cl.
    *G01N 33/00*       (2006.01)
    *G01N 1/22*        (2006.01)
    *G01N 1/40*        (2006.01)
    *B04C 5/20*        (2006.01)

(52) U.S. Cl.
    CPC ....... *G01N 1/4077* (2013.01); *G01N 33/0011* (2013.01)

(56) References Cited

U.S. PATENT DOCUMENTS

| | | | | |
|---|---|---|---|---|
| 4,134,827 | A * | 1/1979 | Frykhult | B04C 5/04 209/729 |
| 4,212,653 | A * | 7/1980 | Giles | B01D 45/16 95/271 |
| 4,216,095 | A * | 8/1980 | Ruff | B04C 3/06 210/512.1 |
| 4,317,716 | A * | 3/1982 | Liller | B04C 5/085 209/733 |
| 4,343,707 | A * | 8/1982 | Lucas | B04C 1/00 210/695 |
| 4,363,641 | A | 12/1982 | Finn, III | |
| 4,364,822 | A * | 12/1982 | Rich, Jr. | B04C 5/13 209/729 |
| 4,842,145 | A * | 6/1989 | Boadway | B04C 5/28 210/512.1 |
| 4,865,633 | A * | 9/1989 | Stevenson | B04C 5/04 55/393 |
| 5,071,557 | A * | 12/1991 | Schubert | B04C 5/081 210/512.1 |
| 5,100,552 | A * | 3/1992 | Carroll | B04C 5/081 209/733 |
| 5,108,608 | A * | 4/1992 | Carroll | B04C 5/30 209/730 |
| 5,683,494 | A * | 11/1997 | Altman | B04C 5/04 96/96 |
| 7,238,281 | B2 * | 7/2007 | Su | E03F 5/14 210/170.03 |
| 7,306,639 | B2 | 12/2007 | Wydra et al. | |
| 8,157,895 | B2 * | 4/2012 | Phillips | B04C 5/04 95/271 |
| 8,410,435 | B2 | 4/2013 | Miki et al. | |
| 9,005,325 | B2 | 4/2015 | Smith | |
| 9,744,490 | B1 | 8/2017 | Novosselov et al. | |
| 9,909,956 | B1 | 3/2018 | St Amant, III | |
| 10,695,703 | B2 | 6/2020 | Lee | |
| 2020/0206672 | A1 | 7/2020 | Vallejo et al. | |

FOREIGN PATENT DOCUMENTS

| | | | | |
|---|---|---|---|---|
| CN | 110899008 B | * | 11/2021 | ............ B04C 11/00 |
| DE | 19820174 A1 | | 11/1999 | |
| WO | WO-2011002373 A1 | * | 1/2011 | ........... B01D 21/267 |

OTHER PUBLICATIONS

Chen, Chih-Chieh, et al., "Shift of Aerosol Penetration in Respirable Cyclone Samplers," American Industrial Hygiene Association Journal, 60:6, 1999, pp. 720-729.

Zhang, Pan, et al., "Numerical Investigation on Gas-solid Flow in a Circumfluent Cyclone Separator," Aerosol and Air Quality Research, 19, 2019, pp. 971-980.

Tsai, Chuen-Jinn, et al., "Effect of Deposited Particles and Particle Charge on the Penetration of Small Sampling Cyclones," J. Aerosol Sci., vol. 30, No. 3, 1999, pp. 313-323.

Lin, Chih-Wei, et al., "Effect of Aerosol Loading on Separation Performance of PM2.5 Cyclone Separators," Aerosol and Air Quality Research, 18, 2018, pp. 1366-1374.

\* cited by examiner

CYCLONE AND METHODS OF MANUFACTURE THEREOF

CROSS-REFERENCE TO RELATED APPLICATIONS

This application claims priority to and the benefit of prior-filed, U.S. provisional patent application Ser. No. 62/930,636, filed on Nov. 5, 2019, the entire contents of which are hereby incorporated by reference.

STATEMENT OF GOVERNMENTAL INTEREST

This invention was made with Government support under contract number N00024-13-D-6400, awarded by the Naval Sea Systems Command (NAVSEA). The Government has certain rights in the invention.

BACKGROUND

This disclosure relates to a cyclone and to methods of manufacture thereof. In particular, this disclosure relates to a miniature cyclone for sample collection, concentration and interfacing to a sensor for real time detection of chemicals/biologicals in gases and fluids with particles entrained therein.

In protecting a community from a chemical or biological attack or accident, it is desirable to accurately and rapidly identify released fluids so that impacted individuals can don protective equipment and or retreat to safety. Alternatively, in surveillance applications, it is desirable for users to quickly sample and identify airborne particulates at a site of interest. In environmental and air quality applications, robust measurement of pollutant particle composition is needed to accurately assess health exposures. It is therefore desirable to develop equipment that can expeditiously facilitate detection of fluids of interest.

SUMMARY

Disclosed herein is a cyclone including a hollow cylindrical upper portion including an upper wall and an outer circular wall; and a hollow conical lower portion including an inclined wall and a base wall; the base wall and the inclined wall being in continuous contact with each other; where the hollow cylindrical portion includes an inlet port; and an outlet port; where the inlet port is operative to permit a fluid with particles entrained therein into the hollow cylindrical upper portion and wherein the outlet port is operative to permit the fluid devoid of a portion of the particles to exit the cyclone; and wherein the upper wall includes a conduit that is operative to permit communication with an analytical device; and wherein the inclined wall of the hollow conical lower portion is in continuous contact with an outer wall of the hollow cylindrical upper portion; wherein total cyclone height H is from about 10 to 30 millimeters; wherein a ratio of total cyclone height H to an inner diameter of the hollow cylindrical upper portion D is from about 0.7 to 1.3 and wherein an angle $\theta$ between an inner surface of the base wall and an inner surface of the inclined wall is from about 110 to 130 degrees.

Also disclosed herein is a method that includes discharging into a cyclone via an inlet port a fluid containing entrained particles; extracting the fluid from an outlet port of the cyclone; where the fluid is devoid of a portion of the entrained particles; and analyzing a biological or chemical composition of the fluid and/or the particles; wherein the cyclone includes a hollow cylindrical upper portion including an upper wall and an outer circular wall; and a hollow conical lower portion including an inclined wall and a base wall; the base wall and the inclined wall being in continuous contact with each other; where the hollow cylindrical portion includes the inlet port; and the outlet port; where the inlet port is operative to permit a fluid with particles entrained therein into the hollow cylindrical upper portion and wherein the outlet port is operative to permit the fluid devoid of a portion of the particles to exit the cyclone; and wherein the upper wall includes a conduit that is operative to permit communication with an analytical device; and wherein the inclined wall of the hollow conical lower portion is in continuous contact with an outer wall of the hollow cylindrical upper portion; wherein total cyclone height H is from about 10 to 30 millimeters; wherein a ratio of total cyclone height H to an inner diameter of the hollow cylindrical upper portion D is from about 0.7 to 1.3 and wherein an angle $\theta$ between an inner surface of the base wall and an inner surface of the inclined wall is from about 110 to 130 degrees.

Also disclosed herein is a method that includes disposing a hollow cylindrical upper portion including an upper wall and an outer circular wall onto a hollow conical lower portion including an inclined wall and a base wall to form a cyclone; hollow cylindrical upper portion includes an inlet port and an outlet port; where the inlet port is operative to permit a fluid with particles entrained therein into the hollow cylindrical upper portion and wherein the outlet port is operative to permit the fluid devoid of a portion of the particles to exit the cyclone; and wherein the upper wall includes a conduit that is operative to permit communication with an analytical device; and wherein the inclined wall of the hollow conical lower portion is in continuous contact with an outer wall of the hollow cylindrical upper portion; wherein total cyclone height H is from about 10 to 30 millimeters; wherein a ratio of total cyclone height H to an inner diameter of the hollow cylindrical upper portion D is from about 0.7 to 1.3 and wherein an angle $\theta$ between an inner surface of the base wall and an inner surface of the inclined wall is from about 110 to 130 degrees.

DETAILED DESCRIPTION

Figure 1:
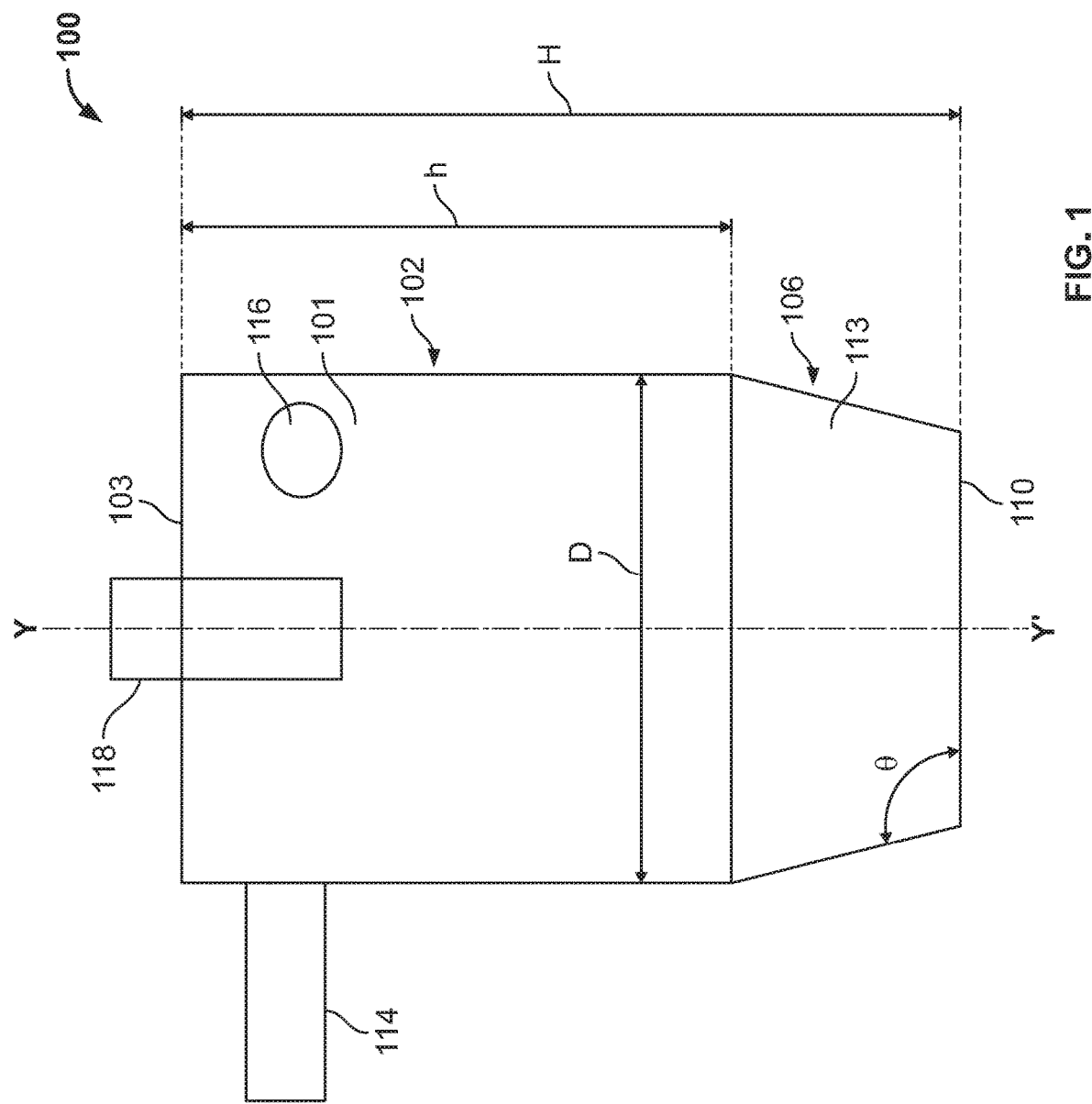
FIG. 1 is an exemplary schematic outline of a cyclone.
Figure 2:
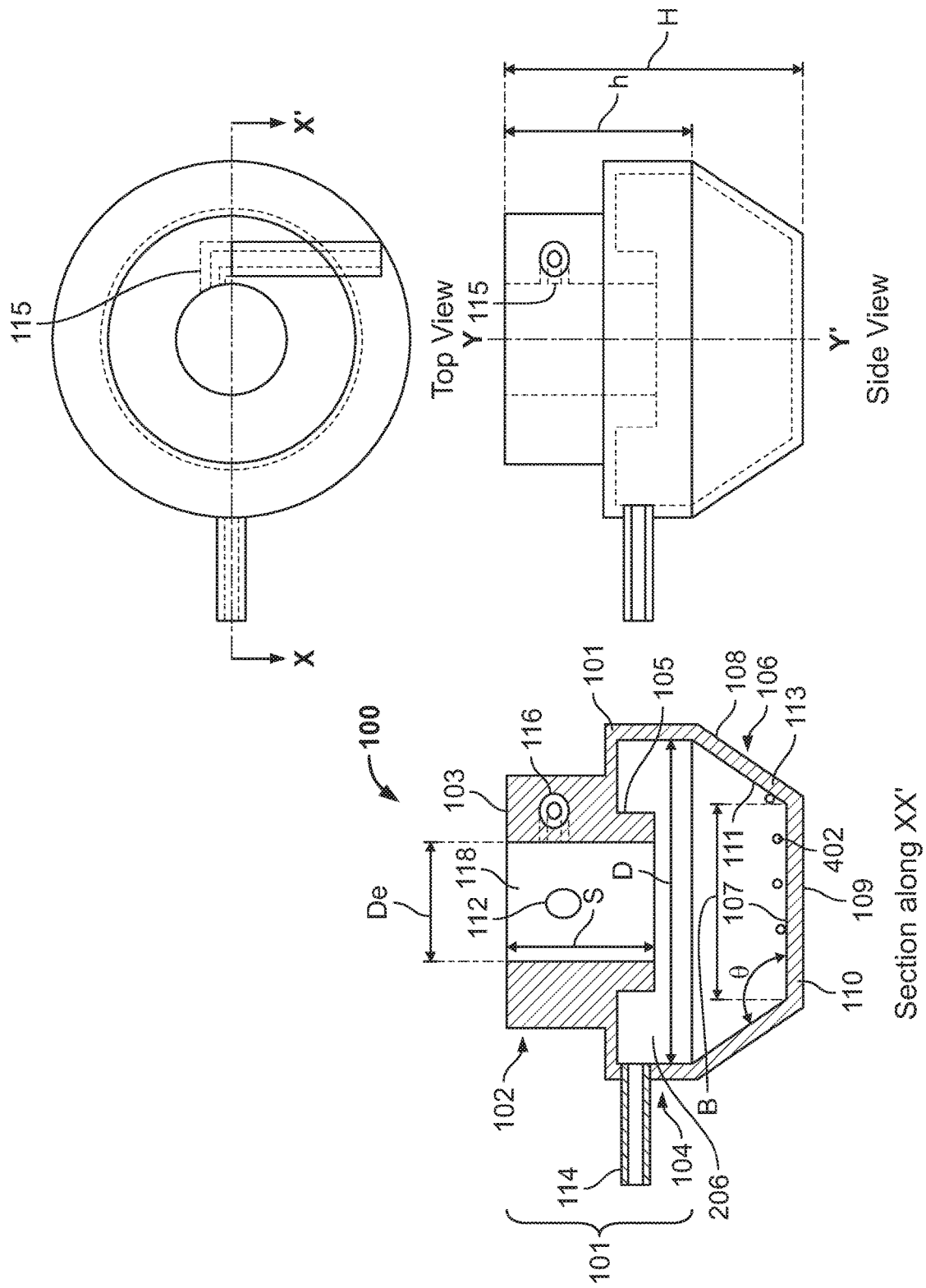
FIG. 2 is a schematic depiction of a side view, top view and sectional view of a cyclone.

It is to be noted that terms such as "higher" and "lower" in reference to the cyclone are made with the understanding that the axis YY' in the FIGS. 1 and 2 is vertical.

Disclosed herein is a cyclone that can be directly interfaced with chemical or biological sensors. The cyclone has dimensions that facilitate efficacious collection of particles contained in a fluid. In an embodiment, the cyclone is a miniaturized cyclone with dimensions in the millimeter or micrometer range. These dimensions (and dimensional ratios between components of the cyclone) are substantially different from the dimensions of other commercially available cyclones resulting in greater collection efficiency as well as detection sensitivity. The cyclone can operate under a wide range of fluid flowrates, allowing for its operation in laminar, transitional, and turbulent flow regimes.

In an example embodiment, the cyclone is a miniature cyclone that operates by forcing particulate-containing fluids to navigate a circular collector geometry, which results in swirling, cyclonic flow patterns for the particles contained in the fluid. Particles contained in fluids with sufficient momentum are unable to follow along the path of fluid as a result of which the particles impinge and are deposited upon the internal walls of the cyclone. In other words, the difference in the mass of the particles from those of the fluid (that the particles are entrained in) cause the particles to experience a greater centrifugal force in the cyclone. This larger centrifugal force causes the particles to deviate from the path of the fluid and to impinge upon and be deposited in small spots on the cyclone walls. These particles captured on the cyclone walls may then be rapidly analyzed by sensors that are in direct contact with the particles or that can remotely access the particles through a capillary tube. In an embodiment, the sensors transmit acquired data to analytical machines which can identify the particles in real time.

FIG. 1 depicts an exemplary schematic outline of a cyclone 100. The cyclone 100 includes a hollow cylindrical upper portion 102 and a hollow conical lower portion 106 that are connected to each other, e.g., they are in continuous contact with each other at their respective outer peripheries, as shown in FIG. 1. In an example embodiment, the hollow cylindrical upper portion 102 and the hollow conical lower portion 106 are formed from the same material, and may be formed from a single piece of the material. The hollow cylindrical upper portion 102 includes an upper wall 103 and an outer circular wall 101. The hollow cylindrical upper portion 102 includes an inlet port 114 that is operative to permit a fluid, which in some cases contains particles entrained therein, into the hollow cylindrical upper portion 102, and an outlet port 116 that permits the fluid, now devoid of at least a portion of the particles, to exit the cyclone 100. The upper wall 103 includes a conduit 118 that is operative to permit communication with an analytical device. The conduit 118 is concentrically situated about a vertical axis YY' with respect to both the hollow cylindrical upper portion 102 and the hollow conical lower portion 106. The conduit 118 is adjacent to the so-called "vortex finder" element of a cyclone's geometry.

The hollow conical lower portion 106 includes an inclined wall 113 and a base wall 110 that are connected, e.g., are in continuous contact with each other. In an example embodiment, the inclined wall 113 and the base wall 110 are formed from the same material, and may be formed from a single piece of the material. It has been discovered that, by maintaining a certain range of a ratio of total cyclone height "H" to inner diameter "D" of the hollow cylindrical upper portion and by maintaining a certain angle "θ" range between an inner surface of the base wall and an inner surface of the inclined wall, the cyclone 100 according to the example embodiments described herein is significantly more efficient than existing cyclones at both capturing particles from a fluid in which they are entrained, as well as in facilitating efficient detection of the composition of the particles.

In one non-limiting, example embodiment, which promotes efficient particle collection and detection from a fluid in which the particles are entrained, the total cyclone height H is from about 10 millimeters to (i.e., including) about 30 millimeters, a ratio of the total cyclone height H to the inner diameter D of the hollow cylindrical upper portion is from about 0.7 to about 1.3, and the angle θ between an inner surface of the base wall 110 and an inner surface of the inclined wall 113 is from about 110 degrees to about 130 degrees. In another example embodiment, the total cyclone height H is from 10 millimeters to 30 millimeters, a ratio of the total cyclone height H to the inner diameter D of the hollow cylindrical upper portion is from 0.7 to 1.3, and the angle θ between an inner surface of the base wall 110 and an inner surface of the inclined wall 113 is from 110 degrees to 130 degrees.

FIG. 2 depicts an exemplary side view, a top view, and a cross-sectional view of the cyclone 100 including the hollow cylindrical upper portion 102 and the hollow conical lower portion 106. The cross-sectional view reflects the view taken at section XX' of the top view. The depictions shown in FIG. 2 are not necessarily to scale. With reference now to the cross-sectional view, the hollow cylindrical upper portion 102 includes the upper wall 103 and the outer circular wall 101. The upper wall 103 includes the conduit 118 through which analytical equipment and accessories for analytical equipment (not shown in FIG. 2) can access collected samples, e.g., samples of gas and/or particles entrained therein flowing through the cyclone 100. The section of the upper wall 103 that contains the conduit 118 has a greater wall thickness than the remainder of the walls for the hollow cylindrical upper portion 102. The portion of the upper wall 103 that includes the conduit also includes an outlet port 116 through which fluids that enter the cyclone can be ejected. The fluids that enter the cyclone can be gases, aerosols, liquids, suspensions, and the like. The gases and liquids may contain entrained particles that may be in solid or liquid form and typically exist in a different phase from the fluid in which they are entrained.

The conduit 118 is concentrically positioned with respect to the hollow cylindrical upper portion 102 and the hollow conical lower portion 106. The lower portion of the conduit 118 protrudes into the hollow cylindrical upper portion 102 and provides a channel 206 between an outer surface 105 of the conduit 118 and an inner surface of the outer circular wall 101. The channel 206 is circular and is concentrically located with respect to the conduit 118. The channel 206 imparts a circular path of travel to fluids that enter the cyclone thus facilitating a separation of the particles from the fluid due to density differences.

The conduit 118 has a height S and diameter $D_e$ such that the ratio of $D_e$ to S is typically less than about 1. The conduit 118 extends a distance equal to the height S from the upper wall 103 to a lower surface of the conduit 118 and acts as a passage through which particles that are separated from the fluid (in the cyclone 100) can be accessed by sensors located inside the conduit or, alternatively, can be transported to an analytical device via a capillary tube (not shown). In an example embodiment, the conduit 118 contains sensors 112 that are in communication with analytical equipment (not shown in the FIG. 2). The sensors 112 can contact separated particulate matter in the cyclone 100 and transmit data to the analytical equipment for analysis. Some embodiments of the communication between the cyclone 100 and analytical equipment are detailed below.

Figure 3:
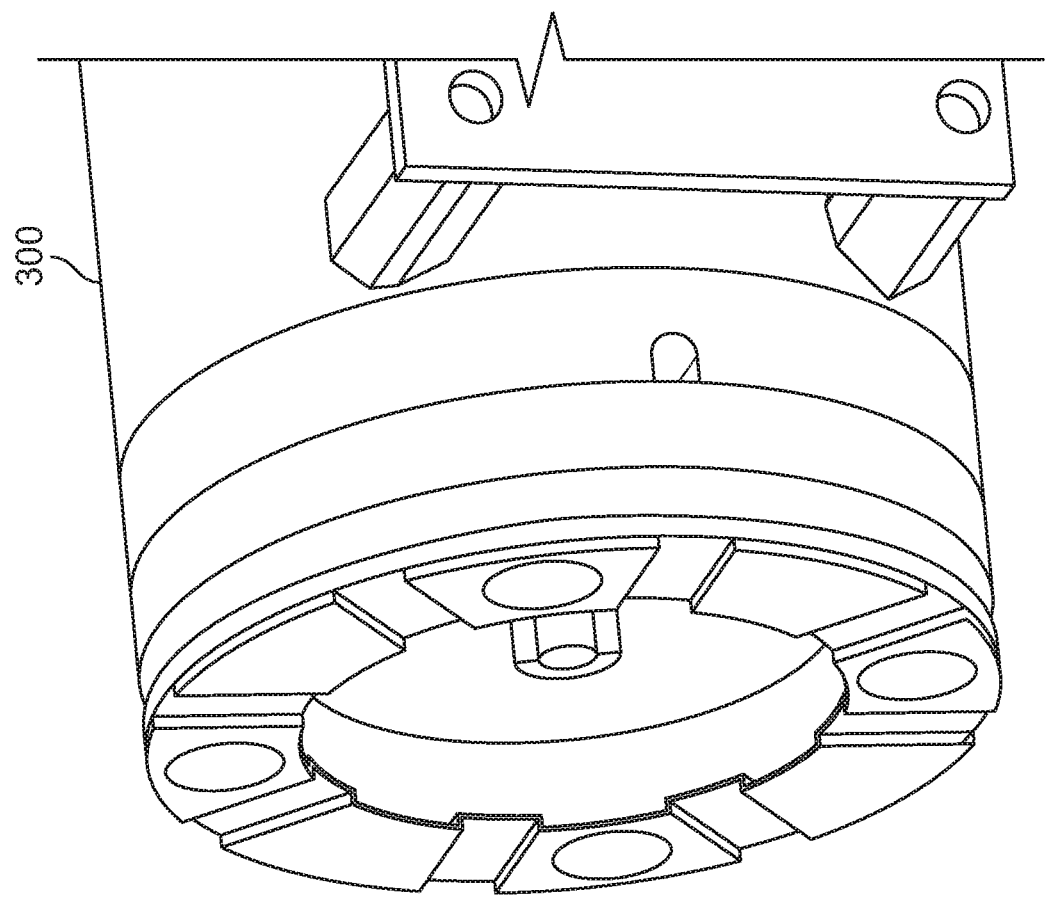
FIG. 3 depicts one mode of connecting a cyclone to an analytical device via an O-ring.
Figure 3:
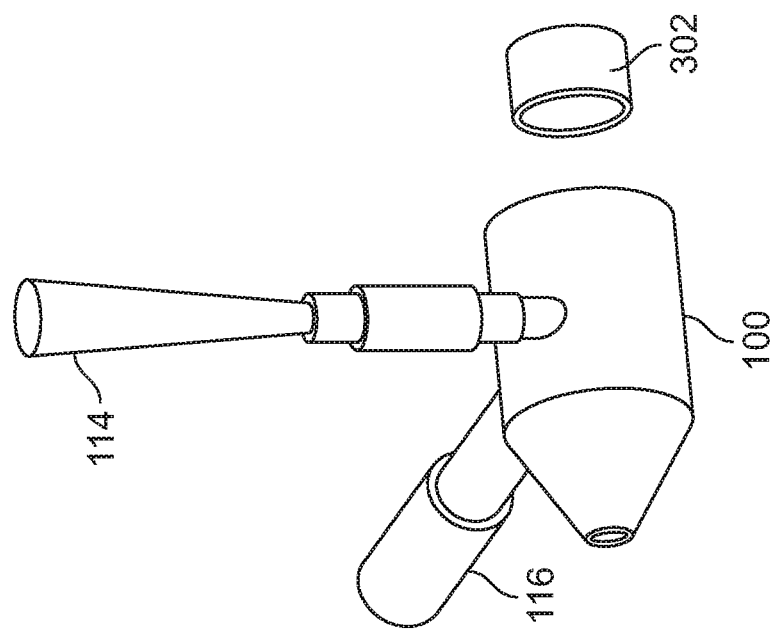

FIG. 3 depicts one mode of connecting the cyclone 100 to an analytical device 300 via, e.g., using, an O-ring 302, for example, though alternative example embodiments are not limited thereto, as any suitable gasket, seal, or other connecting devices may be used in addition to, or as substitutions for, the O-ring 302. In an example embodiment, the cyclone 100 can be removably attached to the analytical device 300 using screws or threads. The O-ring affords a leak proof contact between the cyclone 100 and the analytical device 300.

In one example embodiment, the sensors 112 may be in communication analytical devices through the upper opening in the conduit 118. For example, an optical fiber (not shown) with a sensor at one end thereof can be located in the conduit 118, while the other end of the sensor is in communication with the analytical device. When particles separated from the fluid contact the sensor, a signal transmitted via the optical fiber is analyzed by the analytical device. The sensor 112 can be used to analyze the fluid and/or the particles.

In another example embodiment, the conduit 118 may be used for an air-tight introduction of an analytical probe e.g., a glass capillary tube (not shown) having an outer diameter in a range from about 1 millimeter to about 10 millimeters. In this embodiment, particles separated from the fluid can be transmitted through the capillary tube to the collection chamber of an analytical device where it is sampled and analyzed. It is to be noted that both the fluid and the particles entrained therein can be analyzed as desired.

In yet another example embodiment, a variety of different sensors 112 can be disposed in the conduit 118 via a capillary tube (not shown). In this embodiment, the capillary tube serves as a conduit for transporting particles from the conduit to the chamber and also houses optical fibers which can be used to analyze other components of the fluid.

Analytical techniques such as, for example, mass spectrometry, Raman spectroscopy, laser-induced breakdown spectroscopy, infrared spectroscopy, laser-induced fluorescence, and/or low-temperature plasma mass spectrometry, x-ray photoelectron spectroscopy, Auger electron spectroscopy may be used to analyze particles that are separated or precipitated from a fluid that they are contained in, though alternative example embodiments are not limited thereto. In one example embodiment, the inner surfaces of the cyclone may be functionalized with reactive molecules that can interact with ingredients from the incoming sample and permit analysis of these ingredients. In yet another embodiment, additional concentrators (fluids that facilitate precipitation and concentration of the molecules to be identified) may be introduced into the cyclone (before, during or after an operation) to facilitate analysis using the aforementioned techniques.

With reference once again to FIG. 2, the conduit 118 further contains a port 115 that is in communication with the outlet port 116 through which fluids (now devoid of a portion of the particles contained initially) exit the cyclone.

The hollow cylindrical upper portion 102 is also in communication with an inlet port 114 through which fluids that contain particles (whose identity is to be discovered) enter the cyclone 100. The inlet port 114 is tangentially located in relation to an outer circumference of the hollow cylindrical upper portion 102 and discharges its contents directly into the channel 206 where they are initially confined to a circular path of travel. The inlet port 114 and the outlet port 116 are generally oriented at right angles to each other with the inlet port being located at a lower elevation than the outlet port (when the cyclone axis YY' is oriented vertically).

The hollow upper cylindrical portion 102 has an inner diameter "D" that is greater than the conduit diameter $D_e$. In an example embodiment, the conduit diameter $D_e$ is from about 8 percent (%) to about 15%, and preferably from about 9% to about 12% of the inner diameter D of the hollow cylindrical upper portion 102. In another non-limiting, example embodiment, the conduit diameter $D_e$ is from 9% to 12% of the inner diameter D of the hollow cylindrical upper portion 102.

The hollow conical lower portion 106 is in the form of a truncated cone with its larger diameter wall in continuous contact with the outer circular wall 101. The hollow conical lower portion 106 begins at the point where the hollow cylindrical upper portion 102 ends and is in contact with the hollow cylindrical upper portion 102 at its outer periphery. The hollow conical lower portion 106 includes an inclined wall 113 that contacts a base wall 110 to form a closed space. The inclined wall 113 has an inner surface 111 and an outer surface 108, while the base wall 110 has an inner surface 107 and an outer surface 109. The base wall has an inner diameter "B" as measured where surfaces 107 and 111 intersect. The diameter B is always less than the diameter D and the ratio of B to D generally varies from about 0.15 to about 0.50, and preferably from about 0.20 to about 0.47, and in some example embodiments, from 0.20 to 0.47.

Particles separated from the fluid during their circular path of travel can be collected on the base wall inner surface 107 as well as on other inner surfaces of the cyclone. The base wall 110 meets the inclined wall 113 at an included angle θ as measured between inner surfaces 107 and 111 respectively. The included angle θ can vary from about 110 degrees to about 130 degrees, preferably from about 115 to about 125 degrees and, in one example embodiment, from 115 to 125 degrees.

With reference to the side view and the sectional views of the FIG. 2, the total height of the cyclone (H) (hereinafter referred to as "total cyclone height") is measured from the upper wall 103 of the hollow cylindrical upper portion 102 to the base wall inner surface 107, while the total height of the hollow cylindrical upper portion 102 is denoted by h (hereinafter referred to as total height of the "hollow cylindrical upper portion").

In an example embodiment, by maintaining a ratio of the total height of the cylindrical section to the inner diameter of the larger cylindrical section (h/D) from about 0.35 to about 0.6 (or, alternatively, from 0.35 to 0.6), by maintaining a ratio of the total cyclone height to the inner diameter of the hollow cylindrical upper portion 102 (H/D) from about 0.75 to about 1.3 (or, alternatively, from 0.75 to 1.3) and by maintaining the included angle θ from about 110 degrees to about 130 degrees (or, alternatively, from 110 degrees to 130 degrees), the cyclone can efficiently concentrate fluids containing particles to a small region and therefore improve the sensitivity of analysis.

In one example embodiment, the total cyclone height H can vary from about 10 millimeters to about 30 millimeters, and preferably from about 12 millimeters to about 20 millimeters. The outer diameter of the hollow cylindrical upper portion can vary from about 6 millimeters to about 14 millimeters, and preferably from about 7 millimeters to about 12 millimeters.

In yet another exemplary embodiment, a total cyclone height H is form about 10 millimeters to about 30 millimeters, a ratio of total cyclone height H to an inner diameter D of the hollow cylindrical upper portion 102 is from about 0.7 to about 1.3 (or, alternatively, from 0.7 to 1.3), and an angle θ between an inner surface of the base wall 110 and an inner surface of the inclined wall 113 is from about 110 degrees to about 130 degrees (or, alternatively, from 110 degrees to 130 degrees), which promotes efficient particle collection and detection from a fluid in which they are entrained.

In another example embodiment, for a method of using the cyclone 100, a fluid entrained with particles (whose composition and identity is desired to be determined) is introduced into the inlet port 114. The fluid with the particles contained therein enter the hollow cylindrical upper portion 102 and travel a circular path through channel 206. The greater density of the particles 402 relative to the fluid causes the particles to separate from the fluid and to settle on the inner surfaces of the cyclone. (see FIG. 2) The fluid that is now devoid of a portion of the particles exits the cyclone via outlet port 116. The particles can be analyzed by being transported directly to an analytical device via a capillary tube (not shown) or via a sensor 112 disposed in the conduit 118. The process of separation of the particles from the fluid may be conducted at room temperature or at an elevated temperature by placing the cyclone in an oven or other means.

In one embodiment, microfluidic liquid volumes can be injected into the cyclone to elute/dissolve particles and the solution can then be analyzed via an appropriate chemical or biological assay. In another embodiment, the inlet port of the cyclone can be in communication with chemical concentrators that increase the sensitivity of the system. Chemical concentrators can function to further particle precipitation from the fluid in which they are entrained.

The cyclone may be manufactured by several different methods. The cyclone may be manufactured as a monolith in a single operation (e.g., additive manufacturing) or in several pieces in multiple operations (such as molding, casting, forming, milling, grinding, drilling, welding, and the like) and then assembled together. In an embodiment, the cyclone is manufactured in a combination of manufacturing operations involving additive manufacturing and other operations such as milling, drilling, and micromachining. The parts from the different operations are then polished and assembled together.

The cyclone may be manufactured from a metal, a ceramic, a polymer, or a combination thereof. The material of construction depends upon the fluids being investigated. It is desirable for the material of construction to withstand temperatures at which the separation operations are conducted at. It is also desirable for the material of construction to avoid chemical interactions (e.g., reactions, swelling, and the like) with the fluids or particles being investigated. In an embodiment, the cyclone is manufactured from a metal. In another embodiment, the metal is stainless steel, aluminum, titanium, or a combination thereof.

The cyclone may also be constructed of materials that allow functionalization of molecules or antibodies to the inside surface of the cyclone which then facilitate in-situ biological or chemical assays. For example, during the manufacture of the cyclone, its inner surfaces may be coated with reactive materials that allow functionalization of molecules or antibodies to these surfaces. The surfaces can then be analyzed for the chemical composition of the molecules bonded to the surface. In another embodiment, chemicals are introduced into the cyclone for chemical reactions that facilitate detection.

The cyclone 100 disclosed herein has a number of significant advantages over traditional cyclones. For example, the small size of the cyclone 100 is advantageous in that it permits equivalent or improved fluid or particle collection capabilities compared with other commercially available cyclones. The cyclone 100 permits particle collection and concentration at small spots on the inner surface of the cyclone by using low fluid flow rates. Because of its size, the cyclone 100 may be heated or cooled during collection allowing near-real time analysis of low volatility or extremely volatile aerosols. Sample collection/analysis/detection may be conducted during heating/cooling of the cyclone 100. The modified conduit permits an analysis probe to access the cyclone body while not disturbing the vertical flow dynamics and simultaneously allowing exhaust airflow to exit the cyclone 100.

While the invention has been described with reference to some example embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A cyclone comprising:

a hollow cylindrical upper portion comprising an upper wall and an outer circular wall; and a hollow conical lower portion comprising an inclined wall and a base wall, the base wall and the inclined wall being in continuous contact with each other, wherein the hollow cylindrical upper portion comprises:

an inlet port; and an outlet port, wherein the inlet port is operative to permit a fluid with particles entrained therein into the hollow cylindrical upper portion, the outlet port is operative to permit the fluid devoid of a portion of the particles to exit the cyclone, wherein the upper wall comprises a conduit that is operative to permit communication with an analytical device, the inclined wall of the hollow conical lower portion is in continuous contact with an outer wall of the hollow cylindrical upper portion a total cyclone height H is from about 10 millimeters to about 30 millimeters, a ratio of total cyclone height H to an inner diameter D of the hollow cylindrical upper portion is from about 0.7 to about 1.3, an angle θ between an inner surface of the base wall and an inner surface of the inclined wall is from about 110 degrees to about 130 degrees, the inlet port is tangentially located in relation to an outer circumference of the hollow cylindrical upper portion and discharges its contents directly into a channel formed between an inner surface of the hollow cylindrical upper portion and an outer surface of the conduit, a lower portion of the conduit protrudes into the hollow cylindrical upper portion to provides a channel between an outer surface of the conduit and an inner surface of the outer circular wall, the inlet port and the outlet port are at right angles to each other, and the inlet port is at a lower elevation than the outlet port.

2. The cyclone of claim 1, wherein a ratio of a height to diameter of the hollow cylindrical upper portion (h/D) is 0.35 to 0.6.

3. The cyclone of claim 1, wherein the angle θ is from about 115 degrees to about 125 degrees.

4. The cyclone of claim 1, wherein a sensor is disposed in the conduit.

5. The cyclone of claim 1, wherein the conduit comprises a capillary tube that is in communication with an analytical device.

6. The cyclone of claim 1, wherein an outer diameter of the hollow cylindrical upper portion is from about 6 millimeters to about 14 millimeters.

7. The cyclone of claim 1, wherein
the base wall has an inner diameter B, and
a ratio of B to D is from about 0.15 to about 0.50.

8. The cyclone of claim 1, wherein the conduit has a diameter $D_e$ that is from about 8 percent to about 15 percent of the inner diameter D of the hollow cylindrical upper portion.

9. The cyclone of claim 1, wherein the conduit comprises a sensor that facilitates analysis of at least one of the fluid and the particles.

10. A method comprising:
introducing a fluid containing particles entrained therein into a cyclone via an inlet port of the cyclone;
extracting the fluid from an outlet port of the cyclone, where the fluid extracted from the outlet port is devoid of at least a portion of the particles entrained in the fluid introduced into the cyclone; and
analyzing at least one of a biological composition and a chemical composition of at least one of the fluid and the particles,
wherein the cyclone comprises:
a hollow cylindrical upper portion comprising an upper wall and an outer circular wall; and
a hollow conical lower portion comprising an inclined wall and a base wall, the base wall and the inclined wall being in continuous contact with each other,
wherein the hollow cylindrical upper portion comprises:
the inlet port; and
the outlet port, wherein
the inlet port is operative to permit a fluid with particles entrained therein into the hollow cylindrical upper portion,
the outlet port is operative to permit the fluid devoid of a portion of the particles to exit the cyclone, wherein
the upper wall comprises a conduit that is operative to permit communication with an analytical device,
the inclined wall of the hollow conical lower portion is in continuous contact with an outer wall of the hollow cylindrical upper portion
a total cyclone height H is from about 10 millimeters to about 30 millimeters,
a ratio of total cyclone height H to an inner diameter D of the hollow cylindrical upper portion is from about 0.7 to about 1.3,
an angle θ between an inner surface of the base wall and an inner surface of the inclined wall is from about 110 degrees to about 130 degrees,
the inlet port is tangentially located in relation to an outer circumference of the hollow cylindrical upper portion and discharges its contents directly into a channel formed between an inner surface of the hollow cylindrical upper portion and an outer surface of the conduit,
a lower portion of the conduit protrudes into the hollow cylindrical upper portion to provides a channel between an outer surface of the conduit and an inner surface of the outer circular wall,
the inlet port and the outlet port are at right angles to each other, and
the inlet port is at a lower elevation than the outlet port.

11. The method of claim 10, wherein the analysis is conducted via sensors disposed in the conduit.

12. The method of claim 10, further comprising discharging a portion of at least one of the fluid and the particles via a capillary tube to the analytical device.

13. The method of claim 10, further comprising at least one of heating and cooling the cyclone, wherein sample collection/analysis/detection is conducted during the at least one of the heating and the cooling of the cyclone.

14. The method of claim 10, further comprising introducing chemicals into the cyclone for chemical reactions that facilitate detection.

15. A method comprising:
disposing a hollow cylindrical upper portion comprising an upper wall and an outer circular wall onto a hollow conical lower portion comprising an inclined wall and a base wall to form a cyclone, where the hollow cylindrical upper portion comprises an inlet port and an outlet port, wherein
the inlet port is operative to permit a fluid with particles entrained therein to flow into the hollow cylindrical upper portion,
the outlet port is operative to permit the fluid devoid of a portion of the particles to exit the cyclone,
the upper wall comprises a conduit that is operative to permit communication with an analytical device,
the inclined wall of the hollow conical lower portion is in continuous contact with an outer wall of the hollow cylindrical upper portion,
a total cyclone height H is from about 10 millimeters to about 30 millimeters,
a ratio of the total cyclone height H to an inner diameter D of the hollow cylindrical upper portion is from about 0.7 to about 1.3,
an angle θ between an inner surface of the base wall and an inner surface of the inclined wall is from about 110 to about 130 degrees,
the inlet port is tangentially located in relation to an outer circumference of the hollow cylindrical upper portion and discharges its contents directly into a channel formed between an inner surface of the hollow cylindrical upper portion and an outer surface of the conduit,
a lower portion of the conduit protrudes into the hollow cylindrical upper portion to provides a channel between an outer surface of the conduit and an inner surface of the outer circular wall,
the inlet port and the outlet port are at right angles to each other, and
the inlet port is at a lower elevation than the outlet port.

16. The method of claim 15, further comprising manufacturing the hollow cylindrical upper portion and the hollow conical lower portion via additive manufacturing.

17. The method of claim 16, wherein the cyclone is manufactured as a monolith.

* * * * *